US011452876B2

(12) United States Patent
An et al.

(10) Patent No.: US 11,452,876 B2
(45) Date of Patent: Sep. 27, 2022

(54) DYNAMIC ATRIOVENTRICULAR DELAY OPTIMIZATION

(71) Applicant: Cardiac Pacemakers, Inc., St. Paul, MN (US)

(72) Inventors: Qi An, Blaine, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 253 days.

(21) Appl. No.: 16/694,141

(22) Filed: Nov. 25, 2019

(65) Prior Publication Data

US 2020/0188674 A1 Jun. 18, 2020

Related U.S. Application Data

(60) Provisional application No. 62/779,786, filed on Dec. 14, 2018.

(51) Int. Cl.
*A61N 1/368* (2006.01)
*A61N 1/365* (2006.01)

(52) U.S. Cl.
CPC ....... *A61N 1/3682* (2013.01); *A61N 1/36592* (2013.01); *A61N 1/36842* (2017.08); *A61N 1/36843* (2017.08)

(58) Field of Classification Search
None
See application file for complete search history.

(56) References Cited

U.S. PATENT DOCUMENTS

| 2013/0268017 | A1 | 10/2013 | Zhang et al. |
| 2014/0188184 | A1 | 7/2014 | Maskara et al. |
| 2016/0045736 | A1 | 2/2016 | Fishel |
| 2016/0051823 | A1 | 2/2016 | Maile et al. |
| 2018/0214695 | A1 | 8/2018 | Grenz et al. |

(Continued)

FOREIGN PATENT DOCUMENTS

WO  WO-2020123133 A1  6/2020

OTHER PUBLICATIONS

"International Application Serial No. PCT/US2019/062988, International Preliminary Report on Patentability dated Jun. 24, 2021", 8 pgs.

(Continued)

*Primary Examiner* — Jon Eric C Morales
(74) *Attorney, Agent, or Firm* — Schwegman Lundberg & Woessner, P.A.

(57) ABSTRACT

Systems and methods for monitoring and treating patients with heart failure are discussed. The system may receive patient atrioventricular (AV) conduction characteristic under different heart rates or patient conditions. Stimulation parameters including stimulation timing parameters may be stored in a memory. The system may include a stimulation control circuit configured to determine a parameter update schedule indicating a timing at which to update stimulation parameter using patient AV conduction characteristic, and dynamically update at least a portion of the stored set of stimulation parameters at the determined parameter update schedule. For a specified heart rate or heart rate range, a stimulation parameter may be selected from the set of the stimulation parameters for use during cardiac stimulation.

20 Claims, 6 Drawing Sheets

(56) References Cited

U.S. PATENT DOCUMENTS

2018/0361150 A1\* 12/2018 Ternes ................ A61N 1/3714
2018/0361161 A1\* 12/2018 Ternes ................ A61N 1/3714
2018/0361162 A1    12/2018 Ternes et al.

OTHER PUBLICATIONS

"International Application Serial No. PCT/US2019/062988, International Search Report dated Mar. 9, 2020", 5 pgs.
"International Application Serial No. PCT/US2019/062988, Written Opinion dated Mar. 9, 2020", 6 pgs.

\* cited by examiner

| HR (bpm) | AS | AP |
|---|---|---|
| <60 | -- | -- |
| 60-70 | -- | -- |
| 70-80 | -- | -- |
| 80-90 | -- | -- |
| 90-100 | -- | -- |
| >100 | -- | -- |

FIG. 4A

| HR (BPM) | SUPINE | | SITTING | | STANDING | |
|---|---|---|---|---|---|---|
| | AS | AP | AS | AP | AS | AP |
| <60 | -- | -- | -- | -- | -- | -- |
| 60-70 | -- | -- | -- | -- | -- | -- |
| 70-80 | -- | -- | -- | -- | -- | -- |
| 80-90 | -- | -- | -- | -- | -- | -- |
| 90-100 | -- | -- | -- | -- | -- | -- |
| >100 | -- | -- | -- | -- | -- | -- |

FIG. 4B

| HR (bpm) | DAYTIME | | NIGHTTIME | |
|---|---|---|---|---|
| | AS | AP | AS | AP |
| <60 | -- | -- | -- | -- |
| 60-70 | -- | -- | -- | -- |
| 70-80 | -- | -- | -- | -- |
| 80-90 | -- | -- | -- | -- |
| 90-100 | -- | -- | -- | -- |
| >100 | -- | -- | -- | -- |

FIG. 4C

DYNAMIC ATRIOVENTRICULAR DELAY OPTIMIZATION

CLAIM OF PRIORITY

This application claims the benefit of priority under 35 U.S.C. § 119(e) of U.S. Provisional Patent Application Ser. No. 62/779,786, filed on Dec. 14, 2018, which is herein incorporated by reference in its entirety.

TECHNICAL FIELD

This document relates generally to medical systems and devices, and more particularly, to systems, devices, and methods of electrostimulation for treating heart failure.

BACKGROUND

Congestive heart failure (CHF) is a leading cause of death in the United States and globally. CHF occurs when the heart is unable to adequately supply enough blood to maintain a healthy physiological state. CHF may be treated by drug therapy, or by electrostimulation therapy (e.g., cardiac pacing).

Implantable medical devices (IMDs) have been used to monitor CHF patients and manage heart failure in an ambulatory setting. Some IMDs may include sensors to sense physiological signals from a patient, and detect worsening heart failure, such as heart failure decompensation. Frequent patient monitoring and early detection of worsening heart failure may help improve patient outcome. Identification of patient at an elevated risk of future heart failure events may help provide timely treatment and prevent or reduce hospitalization. Identifying and safely managing the patients at risk of worsening heart failure can avoid unnecessary medical interventions, hospitalization, and reduce healthcare cost.

An IMD may include a pulse generator and electrical circuitry configured to electrically stimulate a heart or other excitable tissue, to help restore or improve the cardiac performance, or to correct cardiac arrhythmias. One example of electrostimulation therapy is cardiac resynchronization therapy (CRT). CRT, typically delivered as biventricular (BiV) pacing or synchronized left ventricle (LV)-only pacing, may be indicated for CHF patients with moderate to severe symptoms and ventricular dyssynchrony. CRT keeps the LV and right ventricle (RV) pumping synchronously by sending electrical stimuli to both the LV and RV. The synchronized stimulation may improve heart pumping efficiency and increase blood flow in some CHF patients. CRT can decrease hospitalization and morbidity associated with worsening heart failure, as well as improvements in quality of life.

SUMMARY

This document discusses, among other things, a patient management system for monitoring and treating patients with heart failure. The system may receive information of patient atrioventricular (AV) conduction characteristic, such as under different heart rates or patient conditions. Stimulation parameters, including stimulation timing parameters such as atrioventricular delay (AVD) values, may be stored in a memory. The system may include a stimulation control circuit configured to determine a parameter update schedule indicating a timing at which to update at least a portion of the set of stimulation parameters using the received information of AV conduction characteristic, and dynamically update at least a portion of the stored set of stimulation parameters at the determined parameter update timing. For a specified heart rate or heart rate range, a stimulation parameter such as an AVD value may be selected from the stored set the stimulation parameters for use during cardiac stimulation.

Example 1 is a medical-device system, comprising a stimulation control circuit configured to: determine a parameter update schedule indicating a timing to update a stimulation parameter using an atrioventricular conduction characteristic of a patient; dynamically update at least a portion of a set of stimulation parameters for the patient including stimulation timing parameters stored in a memory at the determined parameter update timing; and for a specified heart rate or heart rate range, select a stimulation parameter from the set of the stimulation parameters for use during cardiac stimulation.

In Example 2, the subject matter of Example 1 optionally includes a receiver circuit configured to receive atrioventricular conduction information of a patient, and a stimulator circuit configured to deliver cardiac stimulation using the selected stimulation parameter. The stimulation control circuit can be configured to determine the atrioventricular conduction characteristic of the patient using the received atrioventricular conduction information.

In Example 3, the subject matter of any one or more of Examples 1-2 optionally includes the stimulation timing parameters that can include atrioventricular delay (AVD) values, and the atrioventricular conduction characteristic includes intrinsic atrioventricular interval (AVI).

In Example 4, the subject matter of any one or more of Examples 1-3 optionally includes the stimulation control circuit that can be configured to determine the parameter update timing using a variability metric of the atrioventricular conduction characteristic.

In Example 5, the subject matter of Example 4 optionally includes the parameter update timing that can include a parameter update rate. The stimulation control circuit can be configured to reduce the parameter update rate corresponding to a heart rate or heart rate range if the variability metric of the atrioventricular conduction characteristic values is below a variability threshold, and to increase the parameter update rate if the variability metric of the atrioventricular conduction characteristic is above the variability threshold.

In Example 6, the subject matter of any one or more of Examples 1-5 optionally includes the stimulation control circuit that can be configured to: determine values of the atrioventricular conduction characteristic corresponding to a plurality of heart rates; and determine the parameter update timing using a covariability metric between the determined values of the atrioventricular conduction characteristic and the corresponding plurality of heart rates.

In Example 7, the subject matter of Example 6 optionally includes the covariability metric that can include a correlation, and the parameter update timing can include a parameter update rate. The stimulation control circuit can be configured to reduce the parameter update rate if the correlation is below a correlation threshold, and to increase the parameter update rate if the correlation is above the correlation threshold.

In Example 8, the subject matter of Example 6 optionally includes the covariability metric that can include a rate of change of the atrioventricular conduction characteristic relative to a change in heart rate. The parameter update timing can include a parameter update rate. The stimulation control circuit can be configured to reduce the parameter update rate if the rate of change of the atrioventricular conduction characteristic is below a rate threshold, and to increase the parameter update rate if the rate of change of the atrioventricular conduction characteristic is above the rate threshold.

In Example 9, the subject matter of any one or more of Examples 1-8 optionally includes the stimulation control circuit that can be configured to determine the parameter update timing further using information of one or more of: cardiac arrhythmia; cardiac conduction abnormality; or physical activity.

In Example 10, the subject matter of any one or more of Examples 1-9 optionally includes the stimulation control circuit that can be configured to measure the atrioventricular conduction characteristic at the determined parameter update timing, and dynamically update at least a portion of the stimulation timing parameters using the measured atrioventricular conduction characteristic.

In Example 11, the subject matter of Example 10 optionally includes the dynamic update of the at least the portion of the stimulation timing parameters that can include a weighted combination of a historical stimulation timing parameter value and the measured atrioventricular conduction characteristic each scaled by respective weight factors.

In Example 12, the subject matter of Example 11 optionally includes the stimulation control circuit that can be configured to adjust one or more of the weight factors using information of physical activity of the patient.

In Example 13, the subject matter of any one or more of Examples 1-12 optionally includes the stimulation control circuit that can be configured to store in the memory the set of stimulation timing parameters for each of a plurality of heart rates or heart rate ranges.

In Example 14, the subject matter of Example 13 optionally includes the stimulation control circuit that can be configured to store in the memory a stimulation parameter table including the set of stimulation timing parameters and the corresponding plurality of heart rates or heart rate ranges.

In Example 15, the subject matter of any one or more of Examples 1-14 optionally includes the stimulation control circuit that can be configured to: generate, and store in the memory, a regression model between (1) values of the atrioventricular conduction characteristic corresponding to a plurality of heart rates or hear rate ranges and (2) the plurality of heart rates or hear rate ranges; and estimate a value of the atrioventricular conduction characteristic at a specific heart rate using the generated regression model; and dynamically update at least a portion of the stimulation timing parameters using the estimated atrioventricular conduction characteristic.

Example 16 is a method of operating a system to control cardiac stimulation. The method comprises steps of: determining a parameter update timing using an atrioventricular conduction characteristic of a patient; dynamically updating at least a portion of a set of stimulation parameters including stimulation timing parameters stored in a memory at the determined parameter update timing; and for a specified heart rate or heart rate range, selecting a stimulation parameter from the set of the stimulation parameters for use during cardiac stimulation.

In Example 17, the subject matter of Example 16 optionally includes the stimulation timing parameters that can include atrioventricular delay (AVD) values, and the atrioventricular conduction characteristic includes intrinsic atrioventricular interval (AVI).

In Example 18, the subject matter of any one or more of Examples 16-17 optionally includes determining the parameter update timing that can include using a variability metric of the atrioventricular conduction characteristic.

In Example 19, the subject matter of any one or more of Examples 16-18 optionally includes determining the parameter update timing that cam include using a covariability metric between (1) values of the atrioventricular conduction characteristic corresponding to a plurality of heart rates and (2) the plurality of heart rates.

In Example 20, the subject matter of any one or more of Examples 16-19 optionally includes comprising measuring the atrioventricular conduction characteristic at the determined parameter update timing. The dynamically updating at least a portion of a set of stimulation parameters incudes using a weighted combination of (1) a historical stimulation timing parameter value and parameters and (2) the measured atrioventricular conduction characteristic at the determined parameter update timing each scaled by respective weight factors.

In Example 21, the subject matter of Example 20 optionally includes adjusting one or more of the weight factors using information of physical activity of the patient.

In Example 22, the subject matter of any one or more of Examples 16-21 optionally includes delivering cardiac stimulation using the selected stimulation parameter.

Example 23 is a medical-device system that comprises: a stimulation control circuit configured to provide cardiac stimulation signals for delivery to a patient according to a set of stimulation parameters: determine a parameter update schedule indicating a timing at which to update at least a portion of the set of stimulation parameters using an atrioventricular conduction characteristic of the patient; and dynamically update at least the portion of the set of stimulation parameters according to the determined timing.

In Example 24, the subject matter of Example 23 optionally includes the stimulation control circuit that can be configured to dynamically update at least one of a stimulation timing parameter, a number of stimulation electrodes, or a stimulation mode of the cardiac stimulation signals.

In Example 25, the subject matter of Example 24 optionally includes the stimulation mode of the cardiac stimulation signals that can include at least one of a left-ventricle-only pacing mode or a bi-ventricular pacing mode.

In Example 26, the subject matter of any one or more of Examples 23-25 optionally includes the stimulation control circuit that can be configured to, select a stimulation parameter from the set of the stimulation parameters for use during cardiac stimulation to the patient for a specified heart rate or heart rate range.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 4A-4C are diagrams illustrating examples of patient condition-indicated stimulation parameter table for use in dynamic cardiac pacing.

DETAILED DESCRIPTION

Figure 1:
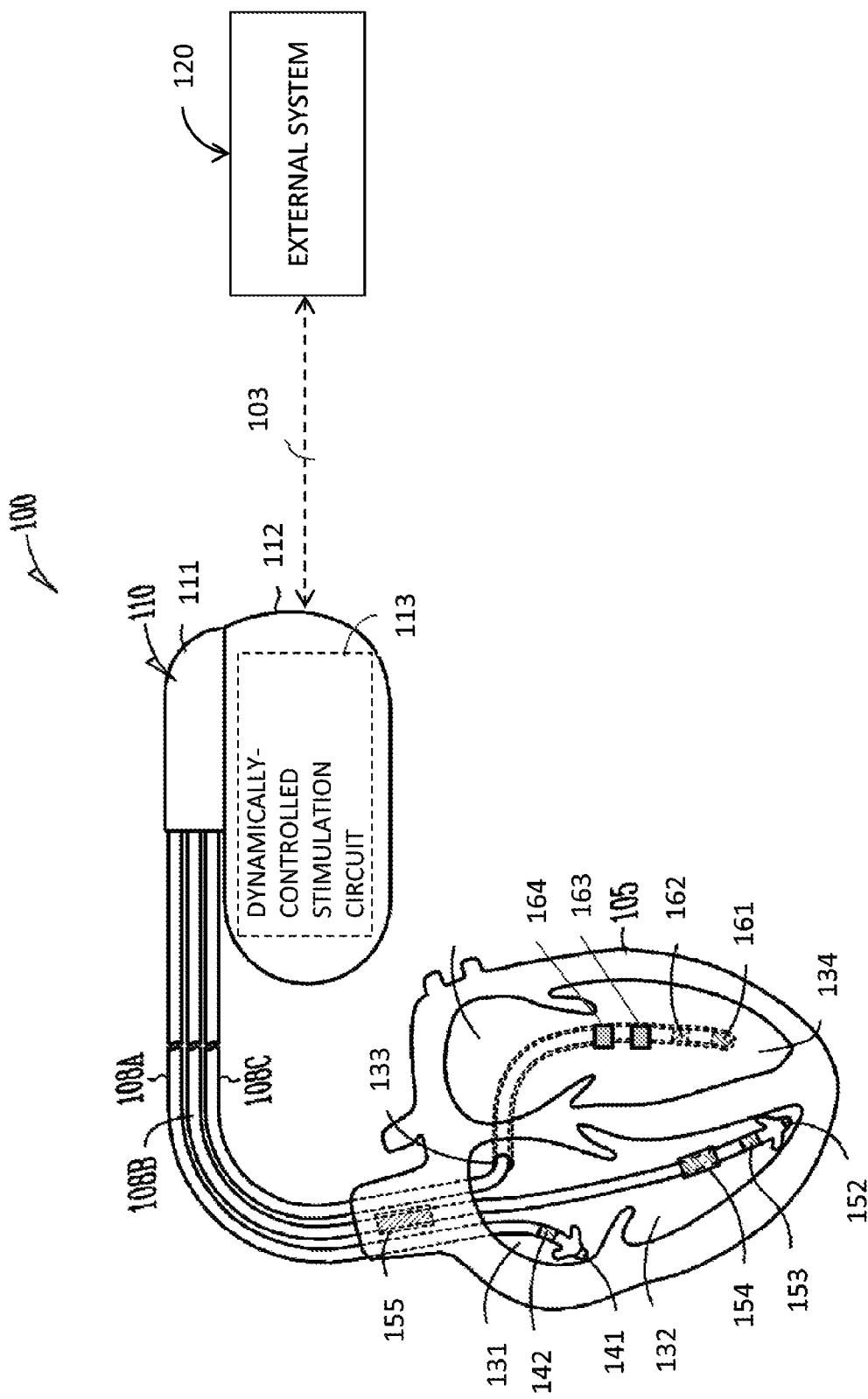
FIG. 1 illustrates an example of a patient management system and portions of an environment in which the system may operate.

Ambulatory medical devices (AMDs), such as IMDs, subcutaneous medical devices, wearable medical devices, or other external medical devices, may be used to detect worsening heart failure and deliver heart failure (HF) therapy to restore or improve the cardiac function. An IMD may be coupled to implanted leads with electrodes that may be used to sense cardiac activity, or to deliver HF therapy, such as cardiac stimulation. An AMD may have functionality of programmable therapy that allows for manual or automatic adjustment of electrostimulation parameters, such as stimulation chamber or site, stimulation mode, or stimulation timing.

An AMD can be configured to stimulation various cardiac chambers to restore cardiac synchrony and improve hemodynamics. During CRT or BiV pacing, synchronized stimulation may be applied to the LV and the RV of a heart. The RV and LV pacing sites may be stimulated concurrently, or sequentially with an RV-LV interventricular pacing delay (VVD). Delivery of LV and RV pacing may be timed relative to a fiducial point, such as an intrinsic atrial depolarization sensed by an atrial electrode (atrial sense, or AS), or an atrial pacing pulse (AP) that elicits atrial activation. If no intrinsic ventricular depolarization is detected within a period of atrial-ventricular delay (AVD) following the AS or the AP, the LV and RV pacing may be delivered at the end of the AVD.

In addition to BiV pacing, stimulation may be delivered only at one heart chamber, such as the LV. The LV-only pacing may improve cardiac synchrony in certain patients, such as those with intact atrioventricular (AV) conduction requiring cardiac resynchronization. Compared to the BiV pacing, LV-only pacing may require a simpler implantable procedure, consumes less power, and provides increased battery longevity. As such, it is clinically a valid alternative to more complicated BiV therapy regime. Similar to timing of BiV pacing, the LV pacing may be delivered at the end of a programmed AVD subsequent to the AS or the AP if no intrinsic LV depolarization is detected within the period of AVD.

An AMD can be configured to stimulate one or more sites of a heart chamber simultaneously or sequentially. In conventional single site pacing (SSP), only one site of a particular heart chamber (e.g., the LV) is stimulated. Alternatively, multisite pacing (MSP) can be used to as an alternative to SSP. The MSP involves electrostimulation at two or more sites in a heart chamber within a cardiac cycle. For example, in LV MSP, multiple LV sites may be simultaneously stimulated, or separated by one or more intra-LV time offset (ILVD). MSP may improve LV function and hemodynamic responses in some patients. However, MSP may require more energy than SSP, and may also increase the complexity of system design and operation. Not all CHF patients can uniformly benefit more from MSP than SSP.

A stimulation timing parameter, such as AVD, VVD, or ILVD discussed above, can determine a timing sequence of cardiac stimulation. Because such timing sequence may affect therapy efficacy and patient hemodynamic outcome, proper selection or programming of a stimulation timing parameter can be important in HF management. For example, AVD can be determined using information about patient intrinsic AV conduction characteristics, such as an intrinsic AV interval (AVI) between a P wave and an R wave within a cardiac cycle in an electrocardiograph (ECG), or between an atrial event (e.g., an atrial sensed (AS) or an atrial paced (AP) event) to a ventricular sensed event (VS) within a cardiac cycle in an subcutaneously measured electrogram (EGM). In a patient, the intrinsic AVI may not stay constant, but vary under a multitude of physiological or functional conditions. For example, long-term changes in patient health conditions, HF progressions such as remodeling or decompensation, or short-term changes in heart rate, postures, posture transitions, physical activities, sleep/awake status, medication, hydration, diet, among other factors, may affect the AVI. As such, cardiac stimulation using a previously optimized AVD may not provide optimal patient outcome under a different patient condition.

The present inventors have recognized a number of technical challenges in cardiac pacing therapy for HF. One challenge has to do with individualized and dynamic HF therapy to address inter-patient differences in cardiac pacing therapy efficacy, as well as intra-patient variations over time in cardiac pacing efficacy at least due to long-term or short-term changes in patient conditions. Timely adjustment of stimulation parameters such as AVD can improve overall therapy efficacy. Another challenge pertains to a guarantee of adequate ventricular pacing therapy (e.g., CRT), particularly in pacing-dependent patients. For example, during therapy optimization to update a stimulation parameter, ventricular pacing therapy may be required to be temporarily suspended. Some conventional pacing systems may reconfigure a pacing electrode (e.g., an LV pacing electrode) to sense cardiac electrical activity during therapy optimization. For example, frequent evaluation of AVI when there is a changing patient condition may require reconfiguring the pacing electrode as a sensing electrode to sense ventricular activation. Frequent electrode reconfiguration may increase pacing system complexity, put a higher demand for computational resources such as firmware cycles, add design and operational cost, and reduce battery life. Suspension of pacing for reassessment of AVI may adversely affect patient outcome.

The present document provides technical solutions to the above-identified challenges in cardiac pacing therapy for HF, and therefore can improve the medical technology of device-based HF management. Among other things, the present document provides apparatus and methods for dynamically updating stimulation parameters, including stimulation timing parameters such as AVD values. The dynamic parameter update discussed herein may also apply to other stimulation parameters, such as for determining a stimulation site or a stimulation mode. The dynamic parameter update can tailor cardiac pacing therapy to an individual patient, as well as to patient physiological or functional conditions. In some examples, the stimulation parameter values (e.g., AVD values) corresponding to a multitude of patient conditions (e.g., heart rates, atrial paced or atrial sensed events, postures) may be stored in a stimulation parameter table. The patient condition-indicated adjustment of stimulation parameter may lead to an individualized pacing therapy to meet patient need. The dynamic adjustment may be specific to a heart rate or heart rate range, or on a beat-to-beat basis. In addition to improved therapy efficacy and patient outcome, the systems and methods discussed herein may also reduce healthcare cost associated with HF management. Additionally, the present document provides identification of the conditions that may affect stimulation timing and therapy efficacy. This may be beneficial for healthcare providers to track patient HF progression, and improve patient management.

This document also discusses a method for determining a parameter update schedule indicating a timing at which to update a stimulation parameter using patient AV conduction characteristic (e.g., intrinsic AVI). At least a portion of the stored set of stimulation parameters can be updated at the determined parameter update schedule. As discussed above, conventionally cardiac pacing therapy may have to be suspended frequently to sense AV conduction characteristic during therapy optimization. This may not only affect patient outcome, but increase device complexity and cost as well. The personalized parameter update timing as discussed in this document can be dynamically determined based on patient condition (e.g., heart rate, AV conduction characteristics, among others). This may not only timely tailor the stimulation parameter and the therapy to patient condition, but also reduce overall pacing suspension time. As a result, both patient outcome and device functionality may be improved.

In addition to the improvement in the medical technology of device-based heart failure patient management under various patient conditions, the systems, devices, and methods discussed herein may also allow for more efficient device memory usage, such as by storing and updating the stimulation timing parameter that are clinically more relevant to patient long-term and short-term changing conditions. In addition to the therapy benefit, the individualized and dynamically adjusted therapy discussed in this document may save device power and extend battery life. With individualized HF therapy tailored to specific patient conditions, fewer unnecessary interventions or hospitalizations may be scheduled, prescribed, or provided; as a result, overall cost savings may be realized.

FIG. 1 illustrates an example of a patient management system 100 and portions of an environment in which the patient management system 100 may operate. The patient management system 100 may include an ambulatory medical device, such as an implantable medical device (IMD) 110 that may be electrically coupled to a heart 105 through one or more leads 108A-C, and an external system 120 that may communicate with the IMD 110 via a communication link 103. Examples of the IMD 110 may include, but are not limited to, pacemakers, defibrillators, CRT devices, cardiac remodeling control therapy (RCT) devices, neuromodulators, drug delivery devices, biological therapy devices, diagnostic devices such as cardiac monitors or loop recorders, or patient monitors, among others. The IMD 110 may be coupled to, or may be substituted by a monitoring medical device such as a bedside or other external monitor. In addition to or in lieu of the IMD 110, other ambulatory medical device may be used, which may include subcutaneous medical device such as a subcutaneous monitor or diagnostic device, or external monitoring or therapeutic medical devices such as automatic external defibrillators (AEDs) or Holter monitors; wearable medical devices such as patch-based devices, smart watches, or smart accessories; or a bedside monitor.

The IMD 110 may include a hermetically sealed can 112 that may house an electronic circuit that may sense a physiological signal in the heart 105 and may deliver one or more therapeutic electrical pulses to a target region, such as in the heart, such as through one or more leads 108A-C. The patient management system 100 may include only one lead such as 108B, or may include two leads such as 108A-B.

The lead 108A may include a proximal end that may be connected to IMD 110 and a distal end that may be placed at a target location such as in the right atrium (RA) 131 of the heart 105. The lead 108A may have a first pacing-sensing electrode 141 that may be located at or near its distal end, and a second pacing-sensing electrode 142 that may be located at or near the electrode 141. The electrodes 141 and 142 may be electrically connected to the IMD 110 such as via separate conductors in the lead 108A, such as to allow for sensing of the right atrial activity and optional delivery of atrial pacing pulses. The lead 108B may be a defibrillation lead that may include a proximal end that may be connected to IMD 110 and a distal end that may be placed at a target location such as in the right ventricle (RV) 132 of heart 105. The lead 108B may have a first pacing-sensing electrode 152 that may be located at distal end, a second pacing-sensing electrode 153 that may be located near the electrode 152, a first defibrillation coil electrode 154 that may be located near the electrode 153, and a second defibrillation coil electrode 155 that may be located at a distance from the distal end such as for superior vena cava (SVC) placement. The electrodes 152 through 155 may be electrically connected to the IMD 110 such as via separate conductors in the lead 108B. The electrodes 152 and 153 may allow for sensing of a ventricular EGM and may optionally allow delivery of one or more ventricular pacing pulses, and electrodes 154 and 155 may allow for delivery of one or more ventricular cardioversion/defibrillation pulses. In an example, the lead 108B may include only three electrodes 152, 154 and 155. The electrodes 152 and 154 may be used for sensing or delivery of one or more ventricular pacing pulses, and the electrodes 154 and 155 may be used for delivery of one or more ventricular cardioversion or defibrillation pulses. The lead 108C may include a proximal end that may be connected to the IMD 110 and a distal end that may be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C may include an electrode 161 that may be located at a distal end of the lead 108C and another electrode 162 that may be located near the electrode 161. The electrodes 161 and 162 may be electrically connected to the IMD 110 such as via separate conductors in the lead 108C such as to allow for sensing the LV EGM and optionally allow delivery of one or more resynchronization pacing pulses from the LV. Additional electrodes may be included in or along the lead 108C. In an example, as illustrated in FIG. 1, a third electrode 163 and a fourth electrode 164 may be included in the lead 108. In some examples (not shown in FIG. 1), at least one of the leads 108A-C, or an additional lead other than the leads 108A-C, may be implanted under the skin surface without being within at least one heart chamber, or at or close to heart tissue.

The IMD 110 may include circuitry that may sense a physiological signal. The physiological signal may include an EGM or a signal representing mechanical function of the heart 105. The hermetically sealed can 112 may function as an electrode such as for sensing or pulse delivery. For example, an electrode from one or more of the leads 108A-C may be used together with the can housing 112 such as for unipolar sensing of an EGM or for delivering one or more pacing pulses. A defibrillation electrode from the lead 108B may be used together with the can housing 112 such as for delivering one or more cardioversion/defibrillation pulses. In an example, the IMD 110 may sense impedance such as between electrodes located on one or more of the leads 108A-C or the can housing 112. The IMD 110 can be configured to inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiological signal may be sensed from one or more physiological sensors that may be integrated within the IMD 110. The IMD 110 may also be configured to sense a physiological signal from one or more external physiological sensors or one or more external electrodes that may be coupled to the IMD 110. Examples of the physiological signal may include one or more of ECG, intracardiac EGM, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiological response to activity, posture, respiration, body weight, or body temperature, among others.

In certain examples, the system 100 may include one or more leadless sensors not being tethered to the IMD 110 via the leads 108A-C. The leadless ambulatory sensors can be configured to sense a physiological signal and wirelessly communicate with the IMD 110. In some examples, the IMD 110 may be a leadless medical device. Unlike a tethered device such as the IMD 110 as illustrated in FIG. 1, a leadless medical device requires no lead, wire, or tether extended between the electrodes and the device body. The leadless medical device may include an anchoring or fixation mechanism for positioning the device body on a target implant side, such as an endocardial surface of one of a left ventricle, a right ventricle, a left atrium, or a right atrium, or an epicardial surface of a portion of the heart. The leadless medical device may be delivered transvenously and positioned within a blood vessel on the heart, such as a coronary vein, where one or more electrodes on the leadless medical device may be directly or indirectly in contact with the epicardial surface of the heart. An example of such an leadless medical device may include the leadless cardiac pacemaker (LCP) disclosed in the commonly assigned U.S. Patent Application Publication US2016/0051823 by Maile et al., entitled "LEADLESS CARDIAC PACEMAKER HAVING A SENSOR WITH A LOWER POWER MODE," which is hereby incorporated by reference in its entirety.

The arrangement and functions of these leads and electrodes are described above by way of example and not by way of limitation. Depending on the need of the patient and the capability of the implantable device, other arrangements and uses of these leads and electrodes are possible.

The patient management system 100 may include a dynamically controlled stimulation circuit 113. The dynamically controlled stimulation circuit 113 may determine therapy parameters dynamically according to patient present physiological or functional conditions. Patient conditions such as patient health status, HF progressions, remodeling or decompensation, heart rate, postures, posture transitions, physical activities, sleep/awake status, medication, hydration, diet, among other factors, may affect cardiac electrical and mechanical properties, and consequently affect HF therapy efficacy. The dynamically controlled stimulation circuit 113 may determine stimulation parameters (e.g., AVD) using the sensor input. In an example, the stimulation parameters may be arranged in a table stored in a memory, along with the corresponding patient physical and physiological conditions. In some examples, the dynamically controlled stimulation circuit 113 may determine a stimulation site such as between a LV-only pacing and a BiV pacing, or a stimulation mode such as between a SSP and MSP, based on the sensor input. The dynamically controlled stimulation circuit 113 may determine a parameter update schedule, such as a timing at which to update a stimulation parameter, using patient AV conduction characteristic, such as intrinsic AVI, and update at least a portion of the stored stimulation parameters at the determined parameter update timing. For a specified heart rate (intrinsic heart rate or atrial paced heart rate) or heart rate range, the dynamically controlled stimulation circuit 113 may select a stimulation parameter (e.g., an AVD value) from the set of the stimulation parameters, and deliver cardiac pacing in accordance with the selected stimulation parameter. Examples of personalized update of stimulation parameter and dynamically controlled cardiac pacing are described below, such as with reference to FIG. 2.

The external system 120 may allow for programming of the IMD 110, and receiving information from the IMD 110, via a communication link 103. The external system 120 may include a local external IMD programmer. The external system 120 may include a remote patient management system that may monitor patient status or adjust one or more therapies such as from a remote location. The remote patient management system may evaluate collected patient data and provide alert notifications, among other possible functions. In an example, the remote patient management system may include a centralized server acting as a central hub for collected patient data storage and analysis. The server can be configured as a uni-, multi- or distributed computing and processing system. The remote patient management system may additionally or alternatively include one or more locally configured clients or remote clients securely connected to the server. Examples of the clients may include personal desktops, notebook computers, mobile devices, or other computing devices. System users, such as clinicians or other qualified medical specialists, may use the clients to securely access stored patient data assembled in the database in the server.

The communication link 103 may include one or more of an inductive telemetry link, a radio-frequency telemetry link, or a telecommunication link, such as an internet connection. The communication link 103 may provide for data transmission between the IMD 110 and the external system 120. The transmitted data may include, for example, real-time physiological data acquired by the IMD 110, physiological data acquired by and stored in the IMD 110, therapy history data or data indicating IMD operational status, programming instructions to the IMD 110 such as to configure the IMD 110 to perform one or more actions including, for example, data acquisition, device self-diagnostic test, or therapy delivery.

The dynamically controlled stimulation circuit 113 may be implemented at the external system 120 such as using data extracted from the IMD 110 or data stored in a memory within the external system 120. Portions of the dynamically controlled stimulation circuit 113 may be distributed between the IMD 110 and the external system 120.

Portions of the IMD 110 or the external system 120 may be implemented using hardware, software, or any combination of hardware and software. Portions of the IMD 110 or the external system 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IMD 110, the patient management system 100 could include a subcutaneous medical device (e.g., subcutaneous ICD, subcutaneous diagnostic device), wearable medical devices (e.g., patch based sensing device), or other external medical devices.

Figure 2:
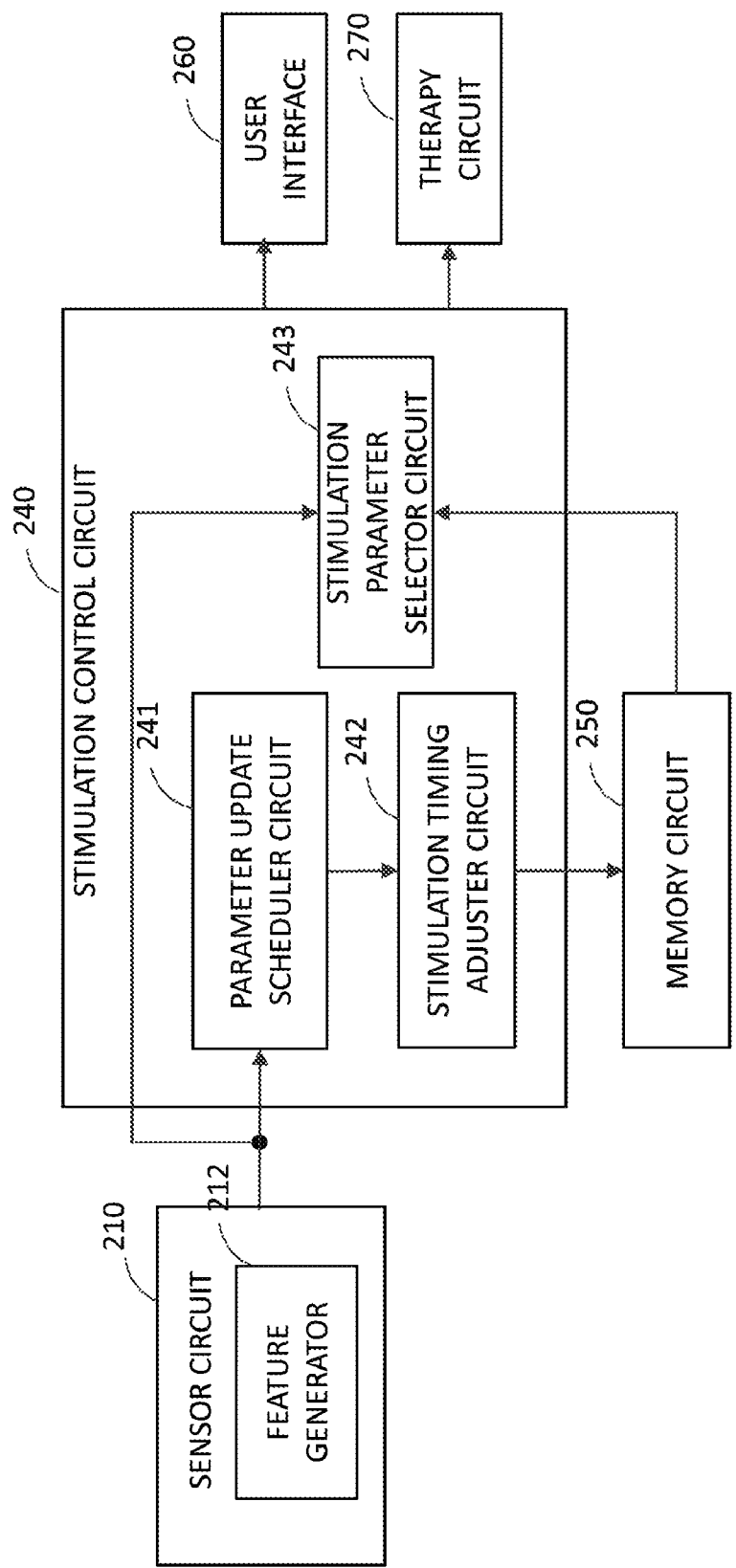
FIG. 2 illustrates an example of a dynamically controlled cardiac stimulation system configured to generate a personalized schedule for updating a stimulation parameter and deliver cardiac stimulation to treat HF or other conditions.

FIG. 2 illustrates an example of a dynamically controlled cardiac stimulation system 200, which can be configured to generate a personalized schedule for updating a stimulation parameter. An example of such a personalized schedule is a parameter update timing that can be determined using patient AV conduction characteristic, or other patient physiological or functional conditions. The system 200 can update the stimulation parameter at a time or an update rate according to the parameter update timing, and select a stimulation parameter for use during cardiac stimulation.

The dynamically controlled cardiac stimulation system 200 may include one or more of a sensor circuit 210, a stimulation control circuit 240, a memory circuit 250, and a user interface 260. In some examples, the system 200 may additionally include a therapy circuit 270 configured to deliver or adjust a therapy, such as a cardiac pacing therapy. At least a portion of the cardiac monitoring system 200 may be implemented in an AMD, such as the IMD 110, or distributed between an AMD or and an external system such as the external system 120.

The sensor circuit 210 may include a sense amplifier to sense a cardiac signal. The cardiac signal may be sensed from different heart chambers, such as one or more of the RA, the RV, the left atrium (LA), or the LV. The cardiac signal may be sensed when the heart undergoes an intrinsic rhythm such as a sinus rhythm, or when the heart is stimulated in accordance with a stimulation protocol, such as pacing at an atrium, a ventricle, or other sites at a specified rate or timing sequence. Examples of the cardiac signal may include cardiac electrical signals such as ECGs sensed non-invasively from body surface, subcutaneous ECGs sensed from subcutaneously placed electrodes, or intracardiac EGMs sensed from electrodes on one or more of the leads 108A-C or the can housing 112. By way of example and not limitation, atrial activation (denoted by AS) may be sensed using a sensing vector comprising one of the atrial electrodes 141 or 142, right ventricular activation (RVS) may be sensed using a sensing vector comprising one of the RV electrodes 152-154, and left ventricular activation (LVS) may be sensed using a sensing vector comprising one of the LV electrodes 161-164.

Additionally or alternatively, the cardiac signals may include signals indicative of cardiac mechanical activities or patient hemodynamic status. In an example, the cardiac signal may include a signal sensed from an accelerometer or a microphone configured to sense heart sounds in a patient. In an example, the cardiac signal may include a cardiac or thoracic impedance signal. The cardiac mechanical signals may include blood pressure sensor signals or any other sensor signals indicative of cardiac mechanical activities or hemodynamic status.

In some examples, the sensor circuit 210 may simultaneously or sequentially sense two or more cardiac signals from different sites of a heart chamber, such as multiple sites at the LV. The sensor circuit 210 may sense LV EGMs from two or more LV sites using respective sensing vectors. An example of the LV sensing vector may include a bipolar sensing vector, such as between a pair of electrodes selected among 161-164. Alternatively, the LV sensing vector may be between one of the electrodes 161-164 and another electrode positioned on a different chamber or on a different lead (e.g., one of 152-155 on the RV lead 108B, or electrodes 141 or 142 on the RA lead 108A). Another example of the LV sensing vector may include a unipolar sensing vector including one of the electrodes 161-164 and the can housing 112.

The sensor circuit 210 may process the sensed cardiac signal, including amplification, digitization, filtering, or other signal conditioning operations. The sensor circuit 210 may include or couple to a feature generator 212 configured to generate a signal feature from the processed cardiac signal. Examples of the signal features may include temporal or morphological features indicative of intrinsic cardiac activity such as a P wave, Q wave, R wave, QRS complex, or T wave that may be detected from a surface ECG, a subcutaneous ECG, or an intracardiac EGM, timing and intensity of evoked cardiac activity such as evoked electrical or mechanical activation in response to an electrostimulation of the heart. Examples of the timing measurement may include a time delay between cardiac activations sensed at different heart chambers (e.g., AVI between an atrium and a ventricle, or RV-LV interval), or between different pacing sites (e.g., sensing delay among various LV sites).

In an example, the feature generator 212 can determine a heart rate using the signal received by the sensor circuit 210. In an example, the heart rate is an intrinsic heart rate in the absence of atrial pacing. In another example, the heart rate is detected during atrial pacing. Such atrial-paced heart rate is substantially equal to atrial pacing rate. The heart rate may be used for scheduling parameter update, such as to determine a parameter update timing. In an example, the parameter update timing includes a parameter update rate. The heart rate may also be used for selecting a stimulation parameter from a set of the stimulation parameters stored in the memory 250. In an example, the feature generator 212 can determine an intrinsic AV conduction characteristic, such as an intrinsic AVI. In an example, the intrinsic AVI may be measured when ventricular pacing (e.g., CRT) is temporarily suspended. In an example, the intrinsic AVI may be determined using a combination of an atrial-to-RV interval ($AV_R$) and an atrial-to-LV interval ($AV_L$). In some examples, AVI may be estimated during pacing, using an offset between an AVD corresponding to a pseudo-fusion beat and a AVI. The offset may be stored in a memory. Under a changing patient condition, the AVI may be estimated using a combination of the AVD that leads to pseudo-fusion and the stored offset. An example of pseudo-fusion based AVI estimation during pacing is disclosed in the commonly assigned U.S. patent application Ser. No. 16/007,094 by Ternes et al., entitled "SYSTEMS AND METHODS FOR DYNAMIC, CONTROL OF HEART FAILURE THERAPY," which is hereby incorporated by reference in its entirety.

In some examples, the sensor circuit 210 may additionally receive information about patient long-term or short-term physiological or functional conditions. Changes in long-term or short-term patient conditions may affect cardiac electrical and mechanical properties and patient hemodynamic responses. As a result, a therapy may be less effective if not timely and properly adjusted to accommodate the changing patient condition. Physiological signals, such as cardiac, pulmonary, neural, or biochemical signals, may be received at the sensor circuit 210. Examples of the physiological signals may include ECG, intracardiac EGM, a heart rate signal, a heart rate variability signal, a cardiovascular pressure signal, a heart sounds signal, a respiratory signal, a thoracic impedance signal, a respiratory sounds signal, or blood chemistry measurements or expression levels of one or more biomarkers. Examples of the functional signals may include patient posture, gait, balance, or physical activity signals, among others. The sensor circuit may sense the functional signals using a motion sensor, such as an accelerometer, gyroscope (which may be a one-, two-, or three-axis gyroscope), magnetometer (e.g., a compass), inclinometers, goniometers, altimeters, electromagnetic tracking system (ETS), or a global positioning system (GPS) sensor, among others. In another example, the functional signal may include information about sleep state signal, such as sleep or awake state, frequency or duration of sleep position switch, sleep incline, or other indicators of sleep quality. In another example, the functional signal may include information on food or drink intake (e.g., swallow), coughing or aspiration detection. In some examples, information about patient physiological or functional conditions may be stored in a storage device, such as an electronic medical record (EMR) system, and the sensor circuit 210 can be configured to receive the patient condition from the storage device in response to a user input or triggered by a specific event.

In some examples, the sensor circuit 210 may receive information about patient medical history, medication intake, hospitalization, surgical procedures, cardiac remodeling, worsening heart failure events such as heart failure decompensation, or HF comorbidities. In some examples, the sensor circuit 210 may receive device implant information, such as position of an implantable lead. For example, an LV lead 108C may be implanted at free wall, anterior, lateral, or posterior, among other possible LV positions. LV lead location may affect the therapy efficacy, and be used for determining the stimulation site, mode, and timing parameter. In some examples, the sensor circuit 210 may additionally include patient echocardiography-derived measurements, such as ejection fraction, cardiac contractility, cardiac timing, or aortic velocity, among other hemodynamic parameters or other clinical diagnostics.

The stimulation control circuit 240 may update one or more stimulation parameters at a specific time or according to a specific update rate, and select a stimulation parameter for use during cardiac stimulation. The stimulation parameters can include one or more stimulation timing parameters, such as an AVD. The stimulation control circuit 240 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The stimulation control circuit 240 may include circuit sets comprising other circuits or sub-circuits, such as one or more of a parameter update scheduler circuit 241, a stimulation timing adjuster circuit 242, and a stimulation parameter selector circuit 243. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The parameter update scheduler circuit 241 can be configured to determine a personalized parameter update schedule, such as a parameter update timing. The parameter update timing may be generated using patient physiological or functional information, such as heart rates or AV conduction characteristics such as received by the sensor circuit 210. In some examples, the stimulation timing parameters (e.g., AVD values) may correspond to a plurality of heart rate ranges. The parameter update scheduler circuit 241 may determine parameter update timing respectively for the plurality of heart rates or heart rate ranges. The parameter update timing for one heart rate range may be different from the parameter update timing for another heart rate range. For example, for a first heart rate range 60-70 bpm, the AVD may be updated at a first rate of once every 10 minutes. For a second heart rate range 80-90 bpm, the AVD may be updated at a second rate of once every 5 minutes. The parameter update timing for the plurality of heart rate ranges may each be determined using AV conduction characteristics measured in corresponding heart rate ranges. Examples of determining a personalized parameter update timing are discussed below, such as with reference to FIG. 3.

The stimulation timing adjuster circuit 242 can be configured to determine or update a stimulation timing parameter using patient physiological or functional information, such as measurements of AV conduction characteristic. The stimulation timing parameter may be determined or updated at a particular time, or at a particular periodic update rate, such as according to the parameter update timing provided by the parameter update scheduler circuit 241. The stimulation timing parameter defines a timing sequence for delivering cardiac stimulation pulses. Examples of the timing parameter may include AVD, VVD, or ILVD. In an example, the stimulation timing adjuster circuit 242 may determine or update AVD using patient intrinsic AVI. The AVI may be measured at the determined parameter update timing. In an example, the stimulation timing adjuster circuit 242 may set a timer with a duration corresponding to the parameter update timing, such as 10 minutes. The timer can be reset to the duration value immediately after an AVI evaluation, and counts down as time elapses thereafter until the timer duration times out, at which another AVI measurement can be made.

The stimulation timing adjuster circuit 242 may determine or update a stimulation timing parameter using a weighted combination of (1) a historical stimulation timing parameter value and (2) the determined value of the AV conduction characteristic, each scaled by respective weight factors. In an example, an AVD may be updated recursively using an intrinsic AVI value as follows:

$$AVD(n)=a*AVD(n-1)+b*AVI(n) \quad (1)$$

where AVD(n) denotes a newly updated AVD value, AVD(n-1) denotes a historical AVD value prior to the update, and AVI(n) denotes a present intrinsic AVI value determined at a time or rate according to the parameter update timing. In an example, the stimulation timing adjuster circuit 242 can adjust one or more of the weight factors "a" or "b" using information of patient physical activity. Intrinsic AVI may change more substantially at a higher physical activity level. AVD may be adjusted to address the activity-indicated change in AVI. In an example, in response to an elevated physical activity level, the stimulation timing adjuster circuit 242 can decrease the weight factor "a" to reduce the impact of historical AVD value, and/or increase the weight factor "b" to increase the sensitivity to the present AVI.

In an example, the stimulation timing adjuster circuit 242 may determine or update AVD using a combination of an AVI measured at the right ventricle ($AV_R$) and an AVI measured at the left ventricle ($AV_L$). The $AV_R$ represents an interval between an atrial sensed (AS) or atrial paced (AP) activation to a sensed RV activation (RVS). The $AV_L$ represents an interval between an AS or an AP activation to a sensed LV activation (LVS). Commonly assigned U.S. patent application Ser. No. 16/007,094 by Ternes et al., entitled "SYSTEMS AND METHODS FOR DYNAMIC CONTROL OF HEART FAILURE THERAPY," discusses a method of determining AVD using a linear combination of $AV_R$ and $AV_L$, which is hereby incorporated by reference in its entirety.

The memory circuit 250 can be configured to store a set of stimulation parameters, such as AVDs. The stimulation timing parameters may correspond to each of a plurality of heart rates or heart rate ranges. In some examples, the stimulation timing parameters may further correspond to other patient conditions such as atrial sensed (AS) events or atrial paced (AP) events, different postures, or different time of a day. The memory circuit 250 can be coupled to the stimulation timing adjuster circuit 242, which can update at least a portion of the stored set of the stimulation parameters with the new values of the stimulation parameter, such as the updated AVD according to Equation (1). When AVDs are respectively determined and stored in the memory for different heart rate or heart ranges, AS or AP events, different postures, or other patient conditions, the stimulation timing adjuster circuit 242 may accordingly update the AVD under corresponding patient conditions, such as by using AVI measured during the corresponding patient condition, according to Equation (1) above. In some examples, the memory circuit 250 may store a stimulation parameter table including stimulation timing parameter values and the corresponding plurality of heart rates or heart rate ranges, optionally with one or more other patient conditions (e.g., postures), or information of time of a day, as illustrated in FIG. 4A-4C below.

The stimulation parameter selector circuit 243, coupled to the memory circuit 250, may select a stimulation parameter from the set of the stimulation parameters stored in the memory, including the dynamically updated stimulating timing parameters provided by the stimulation timing adjustor circuit 242, for use during cardiac stimulation. The stimulation parameter selector circuit 243 may search for a received patient condition (e.g., a heart rate, an AS or AP event, a posture, or a time of a day) from the stored stimulation parameters, and identify a recommended stimulation parameter (e.g., AVD) corresponding to that patient condition.

The stimulation parameter selector circuit 243 may additionally configured to determine a heart chamber, or one or more cardiac sites on a heart chamber, for pacing according to the received patient condition. In an example, the stimulation parameter selector circuit 243 may select between an LV-only pacing and a BiV pacing. The BiV pacing refers to stimulation of both the LV and RV simultaneously or sequentially with a specified time offset. In some patients, the BiV pacing may offer better cardiac synchrony and cardiac contractility than the LV-only pacing configured for only stimulating the LV. However, a change in patient physiological or functional condition (e.g., a heart rate increase, or a posture transition from supine to standing) may alter AV condition, ventricular contractility, or other cardiac properties. Pacing chamber may need to be switched, among other therapy adjustments, to maintain adequate therapy efficacy. The stimulation parameter selector circuit 243 may initiate stimulation site assessment in response to a change of patient condition, and determine between an LV-only pacing and BiV pacing based on a heart rate increase, and an indicator of AV conduction abnormality, such as an extension of AVI or increased irregularity of the AVI.

Additionally or alternatively, the stimulation parameter selector circuit 243 can be configured to determine between a single site pacing (SSP) and a multisite pacing (MSP) according to the received patient condition. The MSP may be delivered at two or more sites inside, or on an epicardial surface of, one or more heart chambers or tissues surrounding any of the chambers. During MSP, pulse trains may be delivered at the two or more cardiac sites simultaneously, or sequentially with an intra-ventricular delay less than a sensed or paced time interval value of the cardiac cycle. The stimulation parameter selector circuit 243 may initiate stimulation mode assessment in response to a change of patient condition, and determine between SSP pacing and a MSP pacing at two or more LV sites using inter-ventricular intervals measured from RV site to various candidate LV sites, such as those corresponding to the LV electrodes 161-164. The inter-ventricular intervals represent degrees of dyssynchrony between RV and various LV sites. The stimulation parameter selector circuit 243 may scan through a plurality of candidate LV electrodes to identify those LV sites with the corresponding inter-ventricular intervals satisfying a specified condition, such as a patient condition-indicated threshold value, and select SSP or MSP based on the candidate electrodes identification. Examples of patient conditioned-indicated stimulation site selection (e.g., between LV-only pacing and BiV pacing) and stimulation mode selection (e.g., between SSP and MSP) as disclosed in the commonly assigned U.S. patent application Ser. No. 16/007,094 by Ternes et al., entitled "SYSTEMS AND METHODS FOR DYNAMIC CONTROL OF HEART FAILURE THERAPY" are hereby incorporated by reference in its entirety.

The user interface 260 may include an input device that enables a system user to program the parameters used for electrostimulation or for sensing the cardiac signals. Examples of the input device may include a keyboard, on-screen keyboard, mouse, trackball, touchpad, touchscreen, or other pointing or navigating devices. The input device may enable the system user to activate automated programming of HF therapy, such as automated determination of stimulation site, stimulation mode, and stimulation timing parameters under a specific patient condition. The input device may also enable the system user to confirm, reject, or otherwise modify the automatically determined therapy programming.

The user interface 260 may include a display for display therapy programming such as automatically determined stimulation site, stimulation mode, and stimulation timing parameters. The output unit 230 may include a printing device for producing a hardcopy of the information. The information may be presented in a table, a chart, a trend, a diagram, or any other types of textual, tabular, or graphical presentation formats. Additional information for displaying may include cardiac signals sensed from the sensor circuit 210, signal features or measurements (e.g., AVI) derived from the sensed cardiac signal, information of patient physiological or functional conditions received from the sensor circuit 210, or device status information such as lead impedance and integrity, battery status such as remaining lifetime of the battery, or cardiac stimulation threshold, or complications associated with stimulation at one or more cardiac sites, among others.

The therapy circuit 270 can be configured to generate therapy according to the parameter values generated and recommended by the stimulation control circuit 240. The therapy may include electrostimulation delivered to the pacing sites via one or more of the leads 108A-C and the respectively attached electrodes. The therapy circuit 270 can be configured to deliver LV-only pacing, or BiV pacing. Additionally or alternatively, the therapy circuit 270 can be configured to generate SSP for stimulating one cardiac site, or a MSP for stimulating two or more sites of the heart within the same cardiac cycle. In an example, the MSP may be delivered within the LV. The LV MSP may have a unipolar pacing configuration where only one electrode (e.g., a cathode) is a LV electrode and the other electrode (e.g., an anode) is the IMD can housing 112. In another example, a true bipolar configuration may be used, where both the cathode and anode are LV electrodes. In yet another example, an extended bipolar configuration may be used, where one electrode (e.g., a cathode) is a LV electrode and the other electrode (e.g., an anode) is a RA electrode such as one of the electrodes 141 or 142, or a RV electrode such as one of the electrodes 152-155. In another example, a tripolar configuration may be used, which may involve two LV electrodes used jointly as a cathode, or two electrodes such as selected from the RA and RV electrodes used jointly as an anode. In an example, one or more LV electrodes may be distributed in one or more LV leads, catheters, or untethered pacing units.

In some examples, the therapy circuit 270 may initiate or adjust electrostimulation at non-cardiac tissues such as nerve tissues, or other therapy types, such as a cardioversion therapy, a defibrillation therapy, or drug therapy including delivering drug to a tissue or organ. In some examples, the therapy circuit 270 may modify an existing therapy, such as adjust a stimulation parameter or drug dosage.

Figure 3:
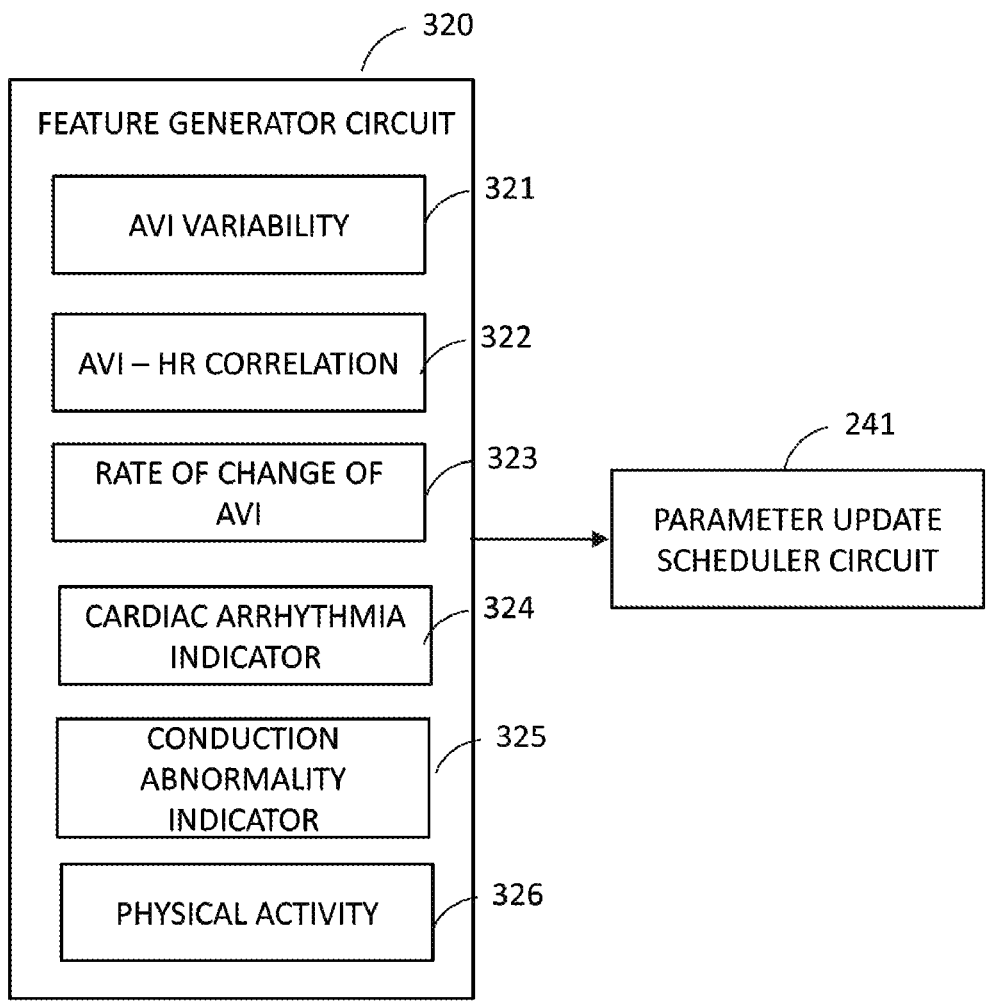
FIG. 3 is a block diagram illustrating an example of a feature generator circuit configured to generate one or more features for use in determining a timing or rate for updating a stimulation parameter.

FIG. 3 is a block diagram illustrating an example of a feature generator circuit 320 configured to generate one or more features for use by the parameter update scheduler circuit 241 to determine a timing or rate for updating a stimulation parameter. The feature generator circuit 320 can be an embodiment of the feature generator circuit 212 of the system 200. In an example, a variability metric of an patient AV conduction characteristic, such as an AVI variability 321, may be generated using values of the AV conduction characteristic. Examples of the variability metric can include range, variance, or standard deviation, among other statistical measures. The parameter update scheduler circuit 241 can reduce the parameter update rate if the variability metric is below a variability threshold, and increase the parameter update rate if the variability metric is above the variability threshold. In an example, the variability metric of the AV conduction characteristic may be compared to one or more thresholds to classify a patient into one of a plurality of variation levels, such as a high variation level, a medium variation level, and a low variation level. The parameter update scheduler circuit 241 can set the parameter update rate to be consistent with the variation level, such that for example the high variation level corresponds to a higher parameter update rate (i.e., more frequent update). In some examples, variability metric of the AV conduction characteristic may be recorded over a period of time, such a specified number of days. The parameter update scheduler circuit 241 can dynamically update the parameter update rate using one or more of the recorded variability metric values.

By way of non-limiting example, an initial parameter update timing may be programmed to update AVD at a pre-determined update rate, such as once every 10 minutes. If the intrinsic AVI is highly variable and exceeds a variability threshold, then the parameter update scheduler circuit 241 can increase the AVD update rate to, for example, once every 8 minutes. However, if the intrinsic AVI measurements is less variable and below the variability threshold, the AVD update rate can remain unchanged, or be reduced to, for example, once every 12 minutes. An increase in AVI variability may be indicative of development of conduction abnormalities, arrhythmias, or other adverse cardiac conditions. More frequent and timely update of AVD can improve cardiac pacing efficacy and patient hemodynamic outcome. Conversely, a less variable AVI may be indicative of stable AV conduction and overall stable cardiac condition. No parameter update or less frequent update may not adversely affect pacing therapy efficacy, and can reduce pacing suspension time (e.g., for reevaluating AVI and updating AVD)

as well as device operation mode switching (e.g., between ventricular pacing and sensing), which can be beneficial to patients particularly those requiring uninterrupted pacing therapy.

In another example, a covariability metric between AV conduction characteristic (e.g., intrinsic AVI) and heart rates may be generated. The AV conduction characteristics may be measured across a range of heart rates. The covariability metric represents a sensitivity of AV conduction characteristic to a change in heart rate. With a higher sensitivity, a moderate fluctuation in heart rate can bring about a substantial change in AVI. Therefore, more frequent AVI reevaluation and AVD update can ensure timely capture of the changes in AVI and adjust the therapy accordingly to meet the patient needs.

An example of the covariability metric is an AVI-HR correlation 322, which can be computed using AVI values and the corresponding heart rates. The parameter update scheduler circuit 241 can reduce the parameter update rate if the correlation is below a correlation threshold, and to increase the parameter update rate if the correlation is above the correlation threshold. Another example of the covariability metric can include a rate of change of AVI 323 relative to a change in heart rate. The parameter update scheduler circuit 241 can reduce the parameter update rate if the relative rate of change of the AV conduction characteristic is below a rate threshold, and to increase the parameter update rate if the relative rate of change of the AV conduction characteristic is above the rate threshold. In an example, the rate of change of AVI 323 may be represented by a slope of a linear regression between values of the AV conduction characteristic and the corresponding heart rates. The parameter update scheduler circuit 241 can reduce the parameter update rate if the slope is below a slope threshold, and to increase the parameter update rate if the slope is above the slope threshold.

The feature generator circuit 320 may additionally or alternatively generate one or more features indicative of changes in heart rhythms or cardiac functions, including for example, an cardiac arrhythmia indicator 324 or a conduction abnormality indicator 325. An episode of a cardiac arrhythmia, or an onset of conduction abnormality (e.g., rate-dependent bundle branch block), may disturb patient intrinsic AVI. Accordingly, the parameter update scheduler circuit 241 can increase the parameter update rate to ensure proper pacing therapy to be delivered to meet patient needs. In another example, the feature generator circuit 320 may generate an indicator of physical activity 326. An increase in physical activity may accelerate heart rate, or trigger rate-dependent conduction abnormalities or certain type of arrhythmias (e.g., sinus tachycardia), thereby introducing changes in patient intrinsic AVI. According, a more frequent AVD update may help ensure timely delivery of proper pacing therapy.

FIGS. 4A-4C are diagrams illustrating patient condition-indicated stimulation parameter values, which can be stored in a memory for dynamic cardiac pacing. The stimulation parameters can be stored in a table, such as table 410, 420, or 430, that includes recommended stimulation timing values along with one or more corresponding patient conditions. Each table entry may include a recommended AVD value under a corresponding patient condition. By way of example and not limitation, FIG. 4A illustrates a stimulation parameter table 410 that includes stimulation timing values, such as AVD values, with corresponding heart rate ranges (HR), and atrial activation mode as either atrial sensed (AS) event or atrial paced (AP) events. The AVD for an AS event is referred to a sensed AVD, and the AVD for an AP event is referred to a paced AVD. FIG. 4B illustrates a stimulation parameter table 420, which is a variant of the Table 410 augmented by patient postures. By way of example, the postures included in the Table 420 include supine, sitting, or standing postures. FIG. 4C illustrates a stimulation parameter table 430, which is another variant of the Table 410 augmented by information of time of a day, such as a daytime or a nighttime. Alternatively, the time of a day may include a number of time periods during a day within a 24-hour period. In various examples, table 410, 420, or 430 may be augmented to include other patient conditions, such as activity (walking or running,) sleeping, diet, hydration, medication intake, heart rate, heart rate variability, arrhythmic events (e.g., atrial fibrillation, ventricular tachycardia, premature ventricular contractions, post arrhythmia). Various combination or permutations of patient conditions can be implemented in a stimulation parameter table similar to the table 310 or 330, which is within the scope of the present document. These patient conditions, individually or in combination, may affect cardiac tissue properties and patient hemodynamics. As a result, a therapy programmed under one condition may not be equally effective under a different condition. Different AVD values may be recommended at different patient conditions to achieve desirable therapy efficacy and patient outcome.

In various examples, at least some entries of a stimulation parameter table may additionally or alternatively include recommended values of stimulation timing parameters other than AVD. In an example, the table entry may include a recommended RV-LV delay (VVD) under corresponding patient conditions of heart rate, posture, and atrial activation mode. The VVD represents an offset between an LV pacing pulse and a RV pacing pulse within a cardiac cycle for BiV pacing or CRT therapy such as selected by a system user or determined by the stimulation parameter selector circuit 243. In some examples, the VVD can be set to zero such that LV pacing and RV pacing are simultaneously delivered. In another example, at least some table entries may include a recommended intra-LV time offset (ILVD). The ILVD represents an offset between LV pacing pulses separately delivered at different LV sites within a cardiac cycle when a LV MSP is selected by a system user or determined by the stimulation parameter selector circuit 243. The LV MSP may be delivered via two or more of the LV electrodes 161-164 as illustrated in FIG. 1.

In various examples, the stimulation parameter table may be augmented to include information in addition to the stimulating timing parameters. In an example, at least some entries of Tables 410-430 may additionally or alternatively include information about stimulation site such as an indication of LV-only pacing or a BiV pacing, or information about stimulation mode such as an indication of SSP or MSP. The augmented table thus provides comprehensive therapy recommendations on stimulation site, mode, and timing values at various patient conditions. In an example, the entries of the augmented table may be constructed as a class structure in the memory circuit 250 that contains values of one or more of the stimulation site, mode, and timing parameters. For example, one table entry may include (AVD, LV-only pacing), and another table entry may include (AVD, BiV pacing, VVD, MSP, ILVD). In an example, one element in a table entry (e.g., AVD value, BiV pacing, or MSP) may be applied to a number of table entries that share a common condition. For example, if BiV pacing is recommended for a condition defined by sitting posture, AS, and HR great than 100 bpm, then BiV pacing may be recommended for all conditions as long as containing a "sitting" posture, regardless of heart rate ranges, or atrial activation mode (AS or AP). In another example, if MSP is recommended for a condition defined by standing posture, AS, and HR within 70-80 bpm, then MSP may be recommended for all conditions as long as containing a "standing" posture, regardless of heart rate ranges, or atrial activation mode.

In some examples, multiple tables of stimulation timing parameter values may be constructed and stored in the memory circuit 250, such as an AVD table containing only AVD values under various patient conditions, a VVD table containing only VVD values under various patient conditions, or an ILVD table containing only ILVD values under various patient conditions. The tables may include different patient physiological or functional conditions. In an example, the stimulation parameter selector circuit 243 may refer to the VVD table to determine an optimal VVD value under a specific patient condition when a BiV pacing is selected. In another example, the stimulation parameter selector circuit 243 may refer to the ILVD table to determine an optimal ILVD value under a specific patient condition when MSP mode is selected. In another example, the stimulation parameter selector circuit 243 may refer to AVD table to determine an optimal AVD under a specific patient condition irrespective of pacing site or pacing mode.

Figure 5:
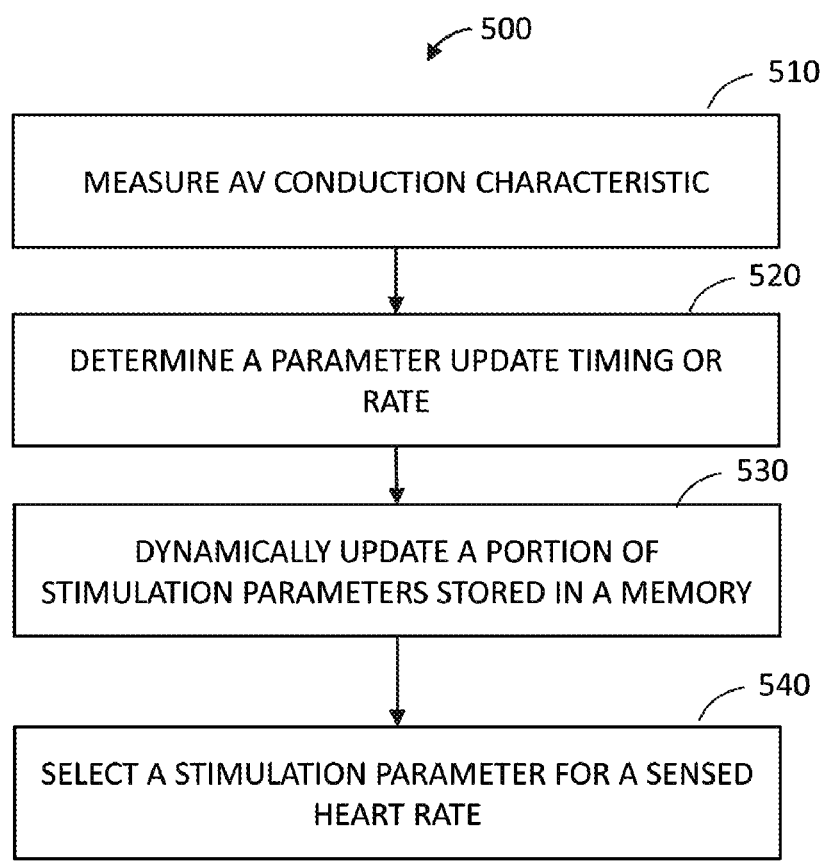
FIG. 5 is a flow chart illustrating a method for updating a stimulation parameter and delivering cardiac stimulation according to the updated stimulation parameter.

FIG. 5 is a flow chart illustrating a method 500 for updating a stimulation parameter and delivering cardiac stimulation according to the updated stimulation parameter. The stimulation parameter, such as a stimulation timing parameter, may be updated at a personalized parameter update timing. The personalized parameter update timing can tailor the stimulation parameters to patient need, and can reduce overall pacing suspension time due to stimulation parameter update. The method 500 can be implemented in and executed by an implant device, such as the IMD 110, or the dynamically controlled cardiac stimulation system 200.

The method 500 commences at 510, where patient atrioventricular (AV) conduction characteristic may be evaluated using cardiac signals, such as received by the sensor circuit 210. Examples of the cardiac signal may include cardiac electrical signals such as surface ECGs, subcutaneous ECGs, or intracardiac EGMs such as sensed from electrodes on one or more of the leads 108A-C or the can housing 112. The cardiac signals may additionally or alternatively include signals indicative of cardiac mechanical activities or patient hemodynamic status. Examples of the AV conduction characteristics can include intrinsic atrioventricular interval (AVI) between an atrial activation (e.g. an atrial sensed (AS) event, or an atrial paced (AP) event) and a ventricular sensed event. The intrinsic AVI may be measured when ventricular pacing is temporarily suspended. In some examples, the intrinsic AVI may be determined using a combination of an AVI measured at the RV (atrial-to-RV interval, $AVI_R$) and an AVI measured at the LV (atrial-to-RV interval, $AVI_R$). In some examples, instead of suspending ventricular pacing to measure AVI directly, AVI may be estimated during pacing, using an offset between an AVD corresponding to a pseudo-fusion beat and a AVI, such as through a testing process. The offset may be stored for future use.

At 520, a personalized parameter update schedule, such as a parameter update timing, can be determined using the measured or otherwise estimated AV conduction characteristic (e.g., AVI) from step 510. In an example, the parameter update timing includes a parameter update rate. In an example, the parameter update timing may be determined or updated using a variability metric of values of the AV conduction characteristic. The parameter update rate can be reduced if the variability metric is below a variability threshold, and increased if the variability metric is above the variability threshold. In an example, the variability metric of the AV conduction characteristic may be compared to one or more thresholds to classify a patient into one of a plurality of variation levels, such as a high variation level, a medium variation level, and a low variation level. The parameter update rate can be set to be consistent with the variation level, such that for example the high variation level corresponds to a higher parameter update rate (i.e., more frequent update). In another example, the parameter update timing may be determined or updated using a covariability metric between (1) values of AV conduction characteristic corresponding to a plurality of heart rates, and (2) the plurality of heart rates. The heart rates can be intrinsic heart rates in the absence of atrial pacing. Alternatively, the heart rates can be acquired during atrial pacing, which are substantially equivalent to atrial pacing rates. The covariability metric represents a sensitivity of AV conduction characteristic (e.g., intrinsic AVI) to a change in heart rate. The covariability can include a correlation between the AVI values and the corresponding heart rates. The parameter update rate can be reduced if the correlation is below a correlation threshold, and increased if the correlation is above the correlation threshold. Alternatively, the covariability metric may be represented by a rate of change of AVI relative to a change in heart rate. The parameter update rate can be reduced if the relative rate of change of the AV conduction characteristic is below a rate threshold, and to increase the parameter update rate if the relative rate of change of the AV conduction characteristic is above the rate threshold. In some examples, the parameter update timing may be determined or updated using information about changes in heart rhythms or cardiac functions, such as cardiac arrhythmias or indications of cardiac conduction abnormalities. The parameter update timing may be determined or adjusted additionally or alternatively using information about physical activity. For example, an increase in physical activity may accelerate heart rate, or trigger rate-dependent conduction abnormalities, thereby introducing changes in patient intrinsic AVI. According, the parameter update rate can be increased so that a more frequent AVD update may help ensure timely delivery of proper pacing therapy.

In some examples, a plurality of parameter update timings may be determined respectively for a plurality of heart rates or heart rate ranges. The parameter update timing for one heart rate or heart rate range may be different from the parameter update timing for another heart rate range. For example, for heart rate range 60-70 bpm, stimulation parameter (e.g., AVD) may be updated at a first rate of once every 10 minutes; yet for heart rate range 80-90 bpm, the AVD may be updated at a second rate of once every 5 minutes. The parameter update timings corresponding to various heart rate ranges may each be determined using signal features (e.g., heart rate, AV conduction characteristics such as AVI) at the corresponding heart rate ranges.

At 530, at least a portion of a set of stimulation parameters stored in a memory can be updated at a particular time or a particular periodic update rate, such as the parameter update timing determined at step 520. A stimulation timing parameter may be updated using patient physiological or functional information, such as measurements of AV conduction characteristic. The stimulation timing parameter defines the timing sequence for delivering cardiac stimulation, and can be important to ensure therapy efficacy and patient hemodynamic response. The timing parameter may include AVD, VVD, or ILVD. In an example, the AVD can be updated using patient intrinsic AVI measured at a time or rate in accordance with the parameter update timing determined at 520. In an example, the AVD can be updated recursively using a weighted combination of (1) a historical stimulation timing parameter value and (2) the determined value of the AV conduction characteristic, such as according to Equation (1) above. In another example, the AVD may be updated using a combination of an AVI measured at the right ventricle ($AV_R$) and an AVI measured at the left ventricle ($AV_L$).

The dynamically updated portion of the set of stimulation parameters can be stored in the memory. The stimulation timing parameters may correspond to each of a plurality of heart rates or heart rate ranges. In some examples, the stimulation timing parameters may further correspond to other patient conditions such as atrial sensed (AS) events or atrial paced (AP) events, different postures, or different time of a day. In some examples, a stimulation parameter table may be created and stored in the memory. The table can include stimulation timing parameter values and the corresponding plurality of heart rates or heart rate ranges, optionally with one or more other patient conditions (e.g., postures), or information of time of a day, as illustrated in FIG. 4A-4C.

At 540, a stimulation parameter can be selected from the set of the stimulation parameters stored in the memory, including the dynamically updated stimulating timing parameters, for use during cardiac stimulation. For a received patient condition (e.g., a heart rate sensed from the patient, an AS or AP event, a posture, or a time of a day), a recommended stimulation parameter (e.g., AVD) corresponding to that patient condition may be identified. Cardiac stimulation (e.g., CRT) may be delivered using the selected stimulation parameter. In various examples, a heart chamber (e.g., LV-only pacing, or BiV pacing of both left and right ventricles), or a pacing mode for pacing a heart chamber (e.g., a single site pacing (SSP), or a multisite pacing (MSP), of a left ventricle), may be determined based on patient condition, as discussed above with reference to FIG. 2.

Figure 6:
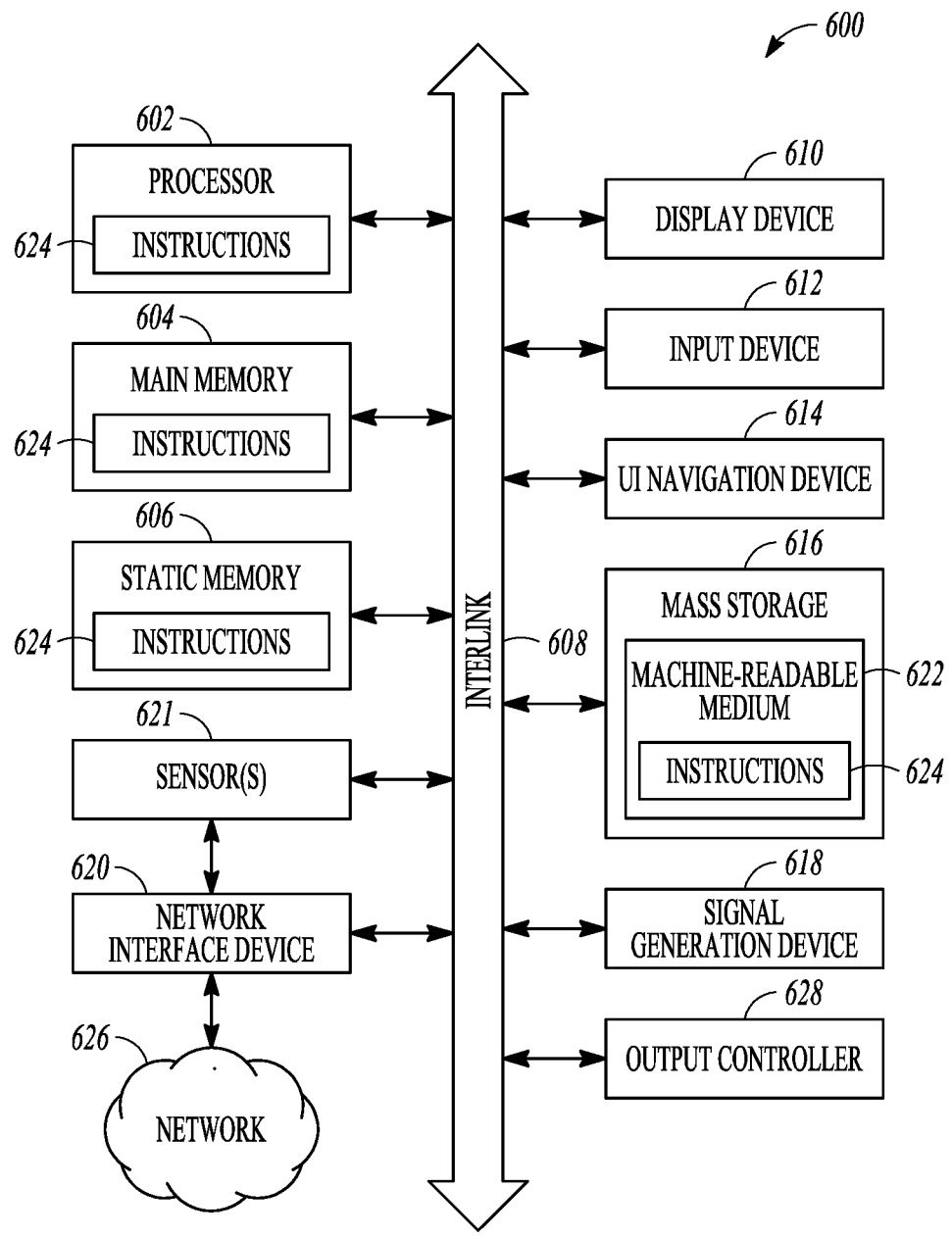
FIG. 6 illustrates a block diagram of an example machine upon which any one or more of the techniques (e.g., methodologies) discussed herein may perform.

FIG. 6 illustrates a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A medical-device system, comprising:
    a stimulation control circuit configured to provide cardiac stimulation signals for delivery to a patient according to a set of stimulation parameters, including:
        determine a parameter update schedule indicating a timing at which to update at least a portion of the set of stimulation parameters using an atrioventricular conduction characteristic of the patient; and
        dynamically update at least the portion of the set of stimulation parameters according to the determined parameter update schedule.

2. The system of claim 1, wherein the stimulation control circuit is configured to dynamically update at least one of a stimulation timing parameter, a number of stimulation electrodes, or a stimulation mode of the cardiac stimulation signals.

3. The system of claim 2, wherein the stimulation mode of the cardiac stimulation signals includes at least one of a left-ventricle-only pacing mode or a bi-ventricular pacing mode.

4. The system of claim 1, wherein the stimulation control circuit is configured to select a stimulation parameter from the set of the stimulation parameters for use during cardiac stimulation to the patient for a specified heart rate or heart rate range.

5. The system of claim 4, comprising:
    a receiver circuit configured to receive atrioventricular conduction information of a patient; and
    a stimulator circuit configured to deliver cardiac stimulation using the selected stimulation parameter,
    wherein the stimulation control circuit is configured to determine the atrioventricular conduction characteristic of the patient using the received atrioventricular conduction information.

6. The system of claim 2, wherein the stimulation timing parameters include atrioventricular delay (AVD) values, and the atrioventricular conduction characteristic includes intrinsic atrioventricular interval (AVI).

7. The system of claim 1, wherein the stimulation control circuit is configured to determine the parameter update schedule using a variability metric of the atrioventricular conduction characteristic.

8. The system of claim 1, wherein the stimulation control circuit is configured to:
    determine values of the atrioventricular conduction characteristic corresponding to a plurality of heart rates; and
    determine the parameter update schedule using a covariability metric between the determined values of the atrioventricular conduction characteristic and the corresponding plurality of heart rates.

9. The system of claim 8, wherein the covariability metric is a rate of change of the atrioventricular conduction characteristic relative to a change in heart rate, the parameter update schedule includes a parameter update rate, and wherein the stimulation control circuit is configured to reduce the parameter update rate if the rate of change of the atrioventricular conduction characteristic is below a rate threshold, and to increase the parameter update rate if the rate of change of the atrioventricular conduction characteristic is above the rate threshold.

10. The system of claim 1, wherein the stimulation control circuit is configured to determine the parameter update schedule further using information of one or more of:
   cardiac arrhythmia;
   cardiac conduction abnormality; or
   physical activity.

11. The system of claim 2, wherein the stimulation control circuit is configured to:
   measure the atrioventricular conduction characteristic at the determined parameter update schedule; and
   dynamically update at least a portion of the stimulation timing parameters using the measured atrioventricular conduction characteristic.

12. The system of claim 11, wherein the dynamic update of the at least the portion of the stimulation timing parameters includes a weighted combination of a historical stimulation timing parameter value and the measured atrioventricular conduction characteristic each scaled by respective weight factors.

13. The system of claim 2, wherein the stimulation control circuit is configured to store in a memory the set of stimulation timing parameters for each of a plurality of heart rates or heart rate ranges.

14. A method of operating a system to control cardiac stimulation, the method comprising:
   determining a parameter update schedule indicating a timing at which to update at least a portion of a set of stimulation parameters using an atrioventricular conduction characteristic of a patient;
   dynamically updating at least a portion of the set of stimulation parameters including stimulation timing parameters stored in a memory at the determined parameter update schedule; and
   for a specified heart rate or heart rate range, selecting a stimulation parameter from the set of the stimulation parameters for use during cardiac stimulation.

15. The method of claim 14, wherein the stimulation timing parameters include atrioventricular delay (AVD) values, and the atrioventricular conduction characteristic includes intrinsic atrioventricular interval (AVI).

16. The method of claim 14, wherein determining the parameter update schedule includes using a variability metric of the atrioventricular conduction characteristic.

17. The method of claim 14, wherein determining the parameter update schedule includes using a covariability metric between (1) values of the atrioventricular conduction characteristic corresponding to a plurality of heart rates and (2) the plurality of heart rates.

18. The method of claim 14, comprising measuring the atrioventricular conduction characteristic at the determined parameter update schedule,
   wherein dynamically updating at least a portion of a set of stimulation parameters incudes using a weighted combination of (1) a historical stimulation timing parameter value and parameters and (2) the measured atrioventricular conduction characteristic at the determined parameter update schedule each scaled by respective weight factors.

19. The method of claim 18, comprising adjusting one or more of the weight factors using information of physical activity of the patient.

20. The method of claim 14, further comprising delivering cardiac stimulation using the selected stimulation parameter.

* * * * *